(12) United States Patent
Corbitt, Jr. et al.

(10) Patent No.: US 6,214,045 B1
(45) Date of Patent: Apr. 10, 2001

(54) BIOABSORBABLE BREAST IMPLANT

(76) Inventors: John D. Corbitt, Jr., 2868 Kirkwood Village, Palm Springs, FL (US) 33461; Lori A. Leonetti, 540 Jefferson Dr., #110, Deerfield Beach, FL (US) 33446

( * ) Notice: Subject to any disclaimer, the term of this patent is extended or adjusted under 35 U.S.C. 154(b) by 0 days.

(21) Appl. No.: 09/169,351

(22) Filed: Oct. 9, 1998

Related U.S. Application Data

(60) Provisional application No. 60/061,588, filed on Oct. 10, 1997, provisional application No. 60/077,639, filed on Mar. 11, 1998, and provisional application No. 60/091,306, filed on Jun. 30, 1998.

(51) Int. Cl.[7] .................. A61F 2/12; A61F 2/02
(52) U.S. Cl. ................. 623/8; 623/23.75; 424/400
(58) Field of Search .................. 623/7, 8, 23.75; 628/8; 606/77; 424/426

(56) References Cited

U.S. PATENT DOCUMENTS

| Re. 35,391 | * | 12/1996 | Brauman | 623/8 |
|---|---|---|---|---|
| 4,298,998 | * | 11/1981 | Naficy | 623/7 |
| 5,120,802 | * | 6/1992 | Mares et al. | 525/415 |
| 5,522,896 | * | 6/1996 | Prescott | 623/6 |
| 5,626,611 | * | 5/1997 | Liu et al. | 606/230 |
| 5,824,081 | * | 10/1998 | Knapp et al. | 623/11 |
| 5,869,080 | * | 2/1999 | McGregor et al. | 424/426 |
| 5,922,024 | * | 7/1999 | Janzen et al. | 623/8 |
| 6,066,325 | * | 5/2000 | Wallace | 424/400 |

OTHER PUBLICATIONS

P. Eiselt et al., "Development of Technologies Aiding Large–Tissue Engineering"; Biotechnology Progress; 1998; vol. 14, No. 1; pp. 134–140.

* cited by examiner

*Primary Examiner*—David H. Willse
*Assistant Examiner*—Suzette J. Jackson
(74) *Attorney, Agent, or Firm*—Ostrolenk, Faber, Gerb & Soffen, LLP

(57) ABSTRACT

A breast implant has at least an outer shell which is composed of a resorbable material. The implant, which can be formed entirely of bioresorbable material, is sized and shaped to replace excised tissue. The implant supports surrounding tissue upon implantation, while allowing for in-growth of fibrous tissue to replace the implant. According to various alternative embodiments, the implant is elastically compressible, or can be formed from self-expanding foam or sponges, and can be implanted through a cannula or by injection, as well as by open procedures. The implant also is capable of carrying therapeutic and diagnostic substances.

24 Claims, 1 Drawing Sheet

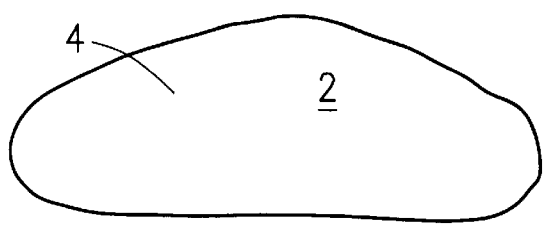
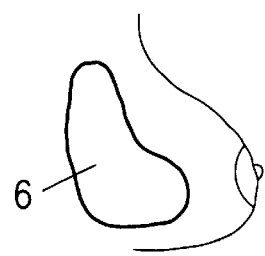
FIG. 1  FIG. 2
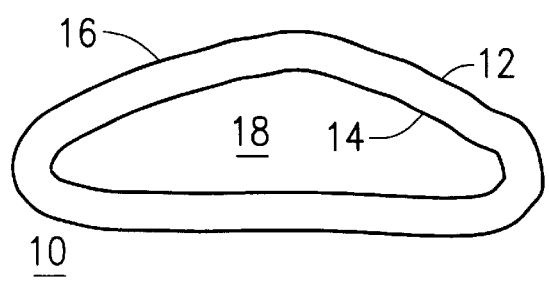
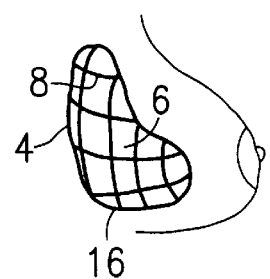
FIG. 4  FIG. 3
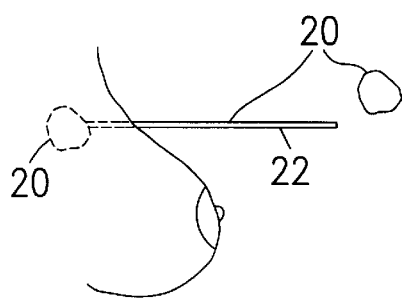
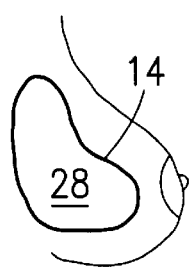
FIG. 6  FIG. 5

BIOABSORBABLE BREAST IMPLANT

This application claims the benefit of U.S. Provisional Application Ser. No. 60/061,588, filed Oct. 10, 1997, U.S. Provisional Application Ser. No. 60/077,639, filed Mar. 11, 1998, and U.S. Provisional Application Ser. No. 60/091,306, filed Jun. 30, 1998, the disclosures of which are incorporated herein by reference.

BACKGROUND OF THE INVENTION

1. Field of the Invention

The present invention relates to implantable prostheses. More particularly, the present invention relates to implantable breast prostheses designed to eliminate encapsulation and reduce scarring, and to replace tissue removed for purposes of biopsy or lumpectomy.

2. Description of the Related Art

Breast prostheses are utilized for augmentation mammoplasty and in cosmetic surgery. Prostheses also are indicated in breast cancer surgery, such as lumpectomies, where a portion of the breast is removed and can leave some disfigurement if not replaced by a similar amount of tissue and/or augmentation material.

Similarly, biopsies can leave small dimples or imperfections if remedial steps are not taken. About 1 million breast biopsies are performed in the United States annually. As a result, some 200,000 new breast cancers are diagnosed each year.

Known methods of augmentation mammoplasty utilize silicone or saline implants. These have been complicated by encapsulation of the implants, which can occur to varying degrees. Encapsulation produces a hard area of scar tissue around the implant, resulting in a rigid, abnormally-shaped mound beneath the breast tissue or pectoralis muscle, depending upon the placement of the implant.

Moreover, the known implant materials may not be indicated for replacement of smaller amounts of tissue, as would be required to prevent dimpling after biopsies, and they are not amenable to resizing. Further, the known implants are not capable of being implanted through a cannula or needle, and are not readily instilled with medicaments or chemical agents that would be useful in treating the patient.

Accordingly, a need exists for implants and methods that can be adapted for replacement of small as well as large amounts of tissue. A need also exists for implants that can be delivered through cannulae or needles, as well as being able to significantly reduce or eliminate encapsulation, resulting in a prolonged, aesthetically pleasing, soft mound below the breast tissue or pectoralis muscle. In addition, a need exists for implants into which useful substances, such as beneficial medications, chemical agents, hormonal treatments, and radiation media can be instilled to enhance the treatment capabilities of the implant in cancer and other breast pathology.

SUMMARY OF THE INVENTION

The present invention overcomes deficiencies of the prior art, such as those noted above, by providing an implant in which at least the outer portion of the implant, and as much the entire implant, is made of a resorbable material. The implant is sized and shaped to replace excised tissue, supports the surrounding tissue after implantation, and permits the in-growth of fibrous replacement tissue without encapsulation or with reduced scarring.

Accordingly, excised tissue is replaced by implanting an implant having at least an outer shell of resorbable material. The implant is sized and shaped to replace the excised tissue. The implant supports surrounding tissue while fibrous tissue replaces the resorbable portion of the implant.

Advantageously, the implant can be provided in the form of a compressible or non-compressible sponge, or a self-expanding foam. The implant can be instilled with beneficial materials, and can be inserted through a cannula, a needle, or directly inserted.

Other features and advantages of the present invention will become apparent from the following description of the invention which refers to the accompanying drawings.

BRIEF DESCRIPTION OF THE DRAWINGS

FIG. 1 is a schematic elevation of a breast implant according to a preferred embodiment of the present invention.

FIG. 2 is a schematic view of a breast after implantation of the implant of FIG. 1.

FIG. 3 is a schematic view of a breast after implantation of an alternative embodiment of the implant of the present invention.

FIG. 4 is a cross-sectional schematic view of a breast implant according to a second alternative embodiment of the present invention.

FIG. 5 is a schematic view of a breast after implantation of the implant of FIG. 4.

FIG. 6 is a schematic view of a breast implant and a method of insertion according to further alternative embodiments of the present invention, particularly for cases involving the removal of smaller pieces of tissue such as by biopsy and lumpectomy.

DETAILED DESCRIPTION OF THE PREFERRED EMBODIMENTS

Referring initially to FIGS. 1 and 2, an implant 2 has an outer shell 4 made of a biosorbable material woven into a mesh. The inner contents of the implant are fluids such as saline and autologous blood products.

Outer shell 4 is made entirely of a biosorbable material, such as polyglycolic acid, for example, as set forth below. Over a period of approximately three weeks to six months, the outer shell will dissolve, leaving the inner contents 6 present inside the breast. Hard encapsulation will not occur because there is not a foreign body contained within the prosthetic space.

Referring to FIG. 3, implantation of an alternative embodiment of implant 2 is illustrated in which the outer shell 4 includes both biosorbable material, and non-absorbable material, such as monofilament polypropylene fibers. Outer shell 4 is provided as a mesh or weave of the mixed material, surrounding contents 6 as described above. After a resorption period, contents 6 remain surrounded by a skeletal outer shell made up of non-absorbable fibers 8, as shown in FIG. 3.

Advantageously, the proportions and spacing of the two types of materials can be altered to provide the desired properties of containment using a minimal amount of non-absorbable material. Accordingly, the non-absorbable fibers 8 which remain after the biosorbable materials resorb will act as a scaffolding to allow the prosthesis to hold its shape; however, because of the limited amount of foreign material, encapsulation and scarring are decreased.

Referring to FIGS. 4 and 5, a second alternative embodiment of the present invention is shown. A prothesis 10 features two capsules, a larger, outer capsule 12 made of biosorbable materials, and a smaller inner capsule 14 made of a non-absorbable material. Inner capsule 14 also can be made partially resorbable as in the first alternative embodiment above. Outer capsule 12 and inner capsule 14 can be separated by a thin layer 16 of saline or autologous fluids such as those described above. Inner capsule 14 surrounds a more permanent prosthesis 18 made of autologous fluids or saline, for example.

After implantation, outer capsule 12 dissolves, thus preventing hardening by encapsulation of the prosthesis. The supply of fluid 16 between the capsules (a few to several cc.'s) is absorbed by the body once released by the dissolution of outer capsule 12.

Referring to FIG. 6, a further alternative embodiment of the present invention includes an implant prosthesis 20 provided in the form of a matrix framework, such as a sponge or foam. The implant, which preferably is entirely biodegradable, has a porous structure which supports the surrounding tissue and provides a framework for the in-growth of fibrous tissue material.

According to a preferred embodiment, the implant is provided in the form of a sponge which can be modified by a surgeon prior to implantation, such as at a lumpectomy or biopsy site, simply by trimming the sponge to the appropriate size and shape. Alternatively, the implant can be a pre-shaped prosthesis of appropriate size, or an appropriate amount of foam. Advantageously, the implant can be modified to correspond to the breast tissue that either has been removed, requires replacement, or requires augmentation.

A preferred method of implantation is shown in FIG. 6, whereby the implant is elastically compressible, and is delivered using a cannula or needle 22 inserted into the breast. A single implant 20 is shown being compressed so as to fit within cannula 22. A force is applied to drive the compressed implant distally through and out the distal end of the cannula into the implant site, where the resilient implant 20 expands to fill the implant site space.

The force for advancing the sponge through the cannula can be applied directly to the implant, or indirectly using fluids, for example. Advantageously, the implant can be used in conjunction with stereotactic biopsy instrumentation, such as the ABBI System, the MIB System by USS, or the Mammotome System.

As a further alternative, the sponge implant of the present invention can form all or part of a larger implant, such as those described above, to form, for example, all or part of the outer shell 4 of implant 2. Implantation using open procedures usually would be indicated when the sponge implant of the present invention is used as all or part of a larger implant. Accordingly, the sponge or implant would be placed directly into the biopsy or lumpectomy cavity.

In addition, the implant 20 can be provided in the form of a self-expanding foam, which can be injected by needle or through cannula 22 in a metered amount. Alternatively, a specialized applicator may be used to inject the desired amount of the foam. The amount of foam is preselected to allow sufficient expansion to fill the void left by the excision and support the surrounding tissue to prevent dimpling.

Following insertion of the implant, such as by an open method or one of the stereotactic methods described above, the resorbable implant occupies the breast tissue cavity and supports the surrounding tissue until such time as it is resorbed or biodegrades. After initial implantation, the patient's own fluids and fibroblast permeate the sponge prosthesis. In the case of a small implant, such permeation would occur naturally, subsequent to implantation. In the case of a larger implant, providing the implant at least partially filled with fluids prior to implantation may be indicated.

Advantageously, the new prosthesis decreases encapsulation after implantation. Various biosorbable materials can be used in the implant of the present invention. Known biosorbable materials include the following:

polyglycolic acid (Dexon, Davis & Geck);

polyglactin material (Vicryl, Ethicon);

poliglecaprone (Monocryl, Ethicon); and synthetic absorbable lactomer 9-1 (Polysorb, United States Surgical Corporation).

The examples above are designed to last varying lengths of time, after which time they are totally resorbed.

According to the present invention, these products may be mixed with one another or combined to provide various resorption times or gradients, and/or may be interrelated with non-absorbable materials, such as polypropylene or PTFFE (Gortex) material, for example. In an instance where a non-absorbable material is utilized, the non-resorbable implant section will remain partially intact as a permanent structure.

In each of the embodiments, the resorbable portions of the prosthesis ultimately biodegrade, and the patient is left with autologous tissue, some of which may have been implanted, or a permanent implant such as saline, as a filler for the biopsy cavity, thus preserving the contour of the breast and preventing indentation of the overlying skin.

The implants of the present invention further can be instilled, before or after implantation, with indicated medicines and other chemical or diagnostic agents. Examples of such agents include, but are not limited to, antibiotics, chemotherapies, other cancer therapies, brachytherapeutic material for local radiation effect, x-ray opaque or metallic material for identification of the area, hemostatic material for control of bleeding, growth factor hormones, immune system factors, gene therapies, biochemical indicators or vectors, and other types of therapeutic or diagnostic materials which may enhance the treatment of the patient.

The present invention has been described particularly in connection with a breast implant, but it will be obvious to those of skill in the art that the invention can have application to other parts of the body, such as the face, and generally to other soft tissue or bone. Accordingly, the invention is applicable to replacing missing or damaged soft tissue, structural tissue or bone, or for cosmetic tissue or bone replacement.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An implant for implantation in a human body comprising an outer shell of resorbable material and a resorbable inner fluid core, the implant being formed to fit the shape and size of a cavity in the human body, the implant being configured to be installed for supporting tissue surrounding the cavity and allowing in-growth of fibrous tissue into and replacing the outer shell.

2. The implant of claim 1, wherein the outer shell further comprises a non-resorbable material.

3. The implant of claim 1, wherein the outer shell is elastically compressible.

4. The implant of claim 1, wherein the core is surrounded completely by the outer shell.

5. The implant of claim 4, wherein the core includes autologous material.

6. The implant of claim 1, further comprising at least one of radiation material, antibiotics, chemotherapies, cancer therapies, hemostatic material, hormone therapies, and radiographic markers.

7. The implant of claim 1, further comprising at least one medicinal, therapeutic or diagnostic substance.

8. The implant of claim 7, wherein the at least one substance is selected from the group consisting of radiation material, antibiotics, chemotherapies, cancer therapies, hemostatic material, hormone therapies, and radiographic markers. and the step of implanting is performed by injection of the self-expanding foam.

9. A method for replacing excised human breast tissue with an implant comprising the steps of:

forming a cavity having surrounding tissue within a breast;

forming the implant entirely of resorbable material and sizing the implant to occupy the cavity; and implanting the implant in the cavity, the implant supporting the surrounding tissue and allowing for in-growth of fibrous tissue into and replacing the resorbable material wherein the resorbable material is elastically compressible, and the step of implanting includes the step of compressing the resorbable material.

10. The method of claim 9, further comprising the step of introducing into the implant at least one of a medicinal, therapeutic or diagnostic substance.

11. The method of claim 9, wherein the at least one substance is selected from the group consisting of radiation material, antibiotics, chemotherapies, cancer therapies, hemostatic material, hormone therapies, and radiographic markers.

12. The implant of claim 1, wherein the core includes a saline solution.

13. The implant of claim 1, further comprising a resorbable inner shell surrounding the inner core, and a supply of fluid disposed between the inner shell and the outer shell.

14. An implant for implantation in a human body comprising an outer shell of a resorbable material, the implant being formed to fit the shape and size of a cavity in the human body, the implant supporting tissue surrounding the cavity upon implantation and allowing for in-growth of fibrous tissue into and replacing the outer shell, and a resorbable core provided inside and surrounded by the outer shell and containing autologous material.

15. The implant of claim 14, wherein the core is partially enclosed by a nonabsorbable material.

16. The method of claim 9, wherein the step of implanting the implant in the cavity comprises expanding the implant within the cavity.

17. A breast implant comprising a self-expanding matrix of biocompatible material, the expanded matrix having a porous structure for supporting surrounding tissue of a breast and configured to provide a framework for the in-growth of fibrous tissue into the matrix.

18. The breast implant of claim 17, wherein the biocompatible material is resorbable.

19. The breast implant of claim 17, wherein the self-expanding matrix comprises a foam.

20. The breast implant of claim 17, wherein the self-expanding matrix comprises a resilient framework for implantation by compressing the matrix into a smaller volume, the matrix expanding resiliently within the breast.

21. The implant of claim 1, wherein the outer shell is adjacent the inner core.

22. A method for replacing excised human breast tissue with an implant comprising the steps of:

forming a cavity having surrounding tissue within a breast;

forming the implant entirely of resorbable material and sizing the implant to occupy the cavity; and implanting the implant in the cavity, the implant supporting the surrounding tissue and allowing for in-growth of fibrous tissue into and replacing the resorbable material, wherein the resorbable material is formed from a self-expanding foam and the step of implanting is performed by injection of the self-expanding foam.

23. The method of claim 22, further comprising the step of introducing into the implant at least one of a medicinal, therapeutic or diagnostic substance.

24. The method of claim 23, wherein the at least one substance is selected from the group consisting of radiation material, antibiotics, chemotherapies, cancer therapies, hemostatic material, hormone therapies, and radiographic markers.

* * * * *

UNITED STATES PATENT AND TRADEMARK OFFICE
CERTIFICATE OF CORRECTION

PATENT NO.   : 6,214,045 B1
DATED        : April 10, 2001
INVENTOR(S)  : John D. Corbitt, Jr. and Lori A. Leonetti It is certified that error appears in the above-identified patent and that said Letters Patent is hereby corrected as shown below:

Claim 8,
Should read as follows:

8. The implant of claim 7, wherein the at least one substance is selected from the group consisting of radiation material, antibiotics, chemotherapies, cancer therapies, hemostatic material, hormone therapies, and radiographic markers.

Signed and Sealed this

Eighteenth Day of December, 2001

*Attest:*

*Attesting Officer*

JAMES E. ROGAN
*Director of the United States Patent and Trademark Office*

(12) EX PARTE REEXAMINATION CERTIFICATE (6465th)
United States Patent
Corbitt, Jr. et al.

(10) Number: US 6,214,045 C1
(45) Certificate Issued: Oct. 7, 2008

(54) BIOABSORBABLE BREAST IMPLANT

(75) Inventors: John D. Corbitt, Jr., Palm Springs, FL (US); Lori A. Leonetti, Deerfield Beach, FL (US)

(73) Assignee: Whitewater Investments, Inc., Atlantis, FL (US)

Reexamination Request:
No. 90/008,109, Jun. 29, 2006

Reexamination Certificate for:
Patent No.: 6,214,045
Issued: Apr. 10, 2001
Appl. No.: 09/169,351
Filed: Oct. 9, 1998

Certificate of Correction issued Dec. 18, 2001.

Related U.S. Application Data

(60) Provisional application No. 60/061,588, filed on Oct. 10, 1997, provisional application No. 60/077,639, filed on Mar. 11, 1998, and provisional application No. 60/091,306, filed on Jun. 30, 1998.

(51) Int. Cl.
*A61F 2/12* (2006.01)
*A61F 2/02* (2006.01)

(52) U.S. Cl. .................. 623/8; 424/400; 623/23.75
(58) Field of Classification Search .................. None
See application file for complete search history.

(56) References Cited

U.S. PATENT DOCUMENTS

| 5,326,350 A | 7/1994 | Li |
| 5,716,404 A | 2/1998 | Vacanti .......................... 623/8 |
| 6,066,325 A | 5/2000 | Wallace et al. |

FOREIGN PATENT DOCUMENTS

| JP | 08-500274 | 1/1996 |
| JP | 09-502371 | 3/1997 |
| WO | WO 94/16647 | 8/1994 |
| WO | WO 95/07057 | 3/1995 |

OTHER PUBLICATIONS

Order Construing Claims of U.S. Patent No. 6,214,045, Civil Action No. CV 04–81178 (S.D. FL).
Rebuttal Expert Report of Dr. Pat Whitworth (prepared by Edward A. Dauer) filed in Civil Action No. CV 04–81178 (S.D. FL).
Letter date Oct. 20, 2004 from EthiconEndo–Surgery to John D. Corbitt, MD, with enclosures.
F. J. O'Brien, et al. "Influence of Freezing Rate on Pore Structure in Freeze–dried Collagen–GAG Scaffolds", *Biomaterials 25* 1077–1086, (2004).
F. J. O'Brien, et al. "The Effect of Pore Size on Cell Adhesion in Collagen–GAG Scaffolds", *Biomaterials 26* 433–441, (2005).
James M. Pachence, "Collagen–based Devices for Soft Tissue Repair", *Journal of Biomedical Materials Research (Applied Biomaterials)* vol. 33, 35–40 (1996).
Jury Verdict Form, Case No. 04–81178–CIV–Middlebrooks/Johnson, *White Water Investments, Inc. v. Ethicon Endo–Surgery, Inc.* (2005).
Court's Instructions to the Jury; Case No. 04–81178–CIV–Middlebrooks/Johnson, *White Water Investments, Inc. v. Ethicon Endo–Surgery, Inc.* (2005).

(Continued)

*Primary Examiner*—Beverly M. Flanagan

(57) ABSTRACT

A breast implant has at least an outer shell which is composed of a resorbable material. The implant, which can be formed entirely of bioresorbable material, is sized and shaped to replace excised tissue. The implant supports surrounding tissue upon implantation, while allowing for in-growth of fibrous tissue to replace the implant. According to various alternative embodiments, the implant is elastically compressible, or can be formed from self-expanding foam or sponges, and can be implanted through a cannula or by injection, as well as by open procedures. The implant also is capable of carrying therapeutic and diagnostic substances.

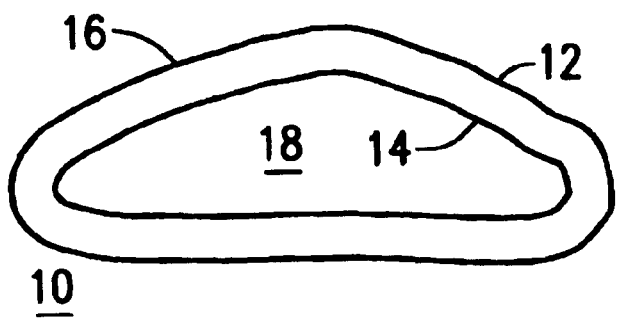
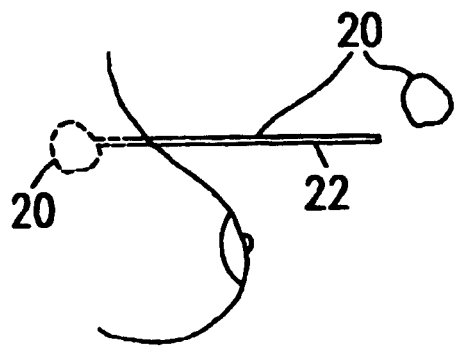

OTHER PUBLICATIONS

Expert Report by Edward A. Dauer, dated Jun. 1, 2005, Case No. 04–81178–CIV–Middlebrooks/Johnson, *White Water Investments, Inc.* v. *Ethicon Endo–Surgery, Inc.*

Defendant's Motion for Summary Judgment, filed Jun. 29, 2005, Case No. 04–81178–CIV–Middlebrooks/Johnson, *White Water Investments, Inc.* v. *Ethicon Endo–Surgery, Inc.*

Declaration of Dr. Pat. Whitworth in Support of Defendant's Motion for Summary Judgment, filed Jun. 29, 2005, Case No. 04–81178–CIV–Middlebrooks/Johnson, *White Water Investments, Inc.* v. *Ethicon Endo–Surgery, Inc.*

Plaintiff's Response in Opposition to Defendant's Motion for Summary Judgment, filed Jul. 18, 2005, Case No. 04–81178–CIV–Middlebrooks/Johnson, *White Water Investments, Inc.* v. *Ethicon Endo–Surgery, Inc.*

Declaration of Dr, Edward A Dauer in Support of Defendant's Motion for Summary Judgment, filed Jul. 18, 2005, Case No. 04–81178–CIV–Middlebrooks/Johnson, *White Water Investments, Inc.* v. *Ethicon Endo–Surgery, Inc.*

Defendant's Reply Memorandum in Support of its Motion for Summary Judgment, filed Jul. 26, 2005, Case No. 04–81178–CIV–Middlebrooks/Johnson, *White Water Investments, Inc.* v. *Ethicon Endo–Surgery, Inc.*

John D. Corbitt, Jr., M.D., "Comparison of the '045 Patent with the Li Patent," filed Jul. 6, 2007.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–24 is confirmed.

New claims 25–28 are added and determined to be patentable.

*25. The method of claim 9, wherein the implant is sized to occupy substantially the entirety of the cavity within the breast.*

*26. The breast implant of claim 17, wherein the implant is sized to occupy substantially an entire cavity in the breast.*

*27. The breast implant of claim 17, wherein the matrix of the implant is configured, in its expanded state, to support the surrounding tissue of the breast.*

*28. The method of claim 22, wherein the implant is sized to occupy substantially the entirety of the cavity within the breast.*

\* \* \* \* \*